United States Patent
Lopizzo

(10) Patent No.: US 11,678,920 B1
(45) Date of Patent: Jun. 20, 2023

(54) BONE SCREW WITH A SLOTTED SELF-DRILLING TIP

(71) Applicant: Graziano Lopizzo, Carlsbad, CA (US)

(72) Inventor: Graziano Lopizzo, Carlsbad, CA (US)

(*) Notice: Subject to any disclaimer, the term of this patent is extended or adjusted under 35 U.S.C. 154(b) by 0 days.

(21) Appl. No.: 17/943,218

(22) Filed: Sep. 13, 2022

(51) Int. Cl.
*A61B 17/86* (2006.01)
*A61B 17/16* (2006.01)

(52) U.S. Cl.
CPC ........ *A61B 17/8635* (2013.01); *A61B 17/864* (2013.01); *A61B 17/1615* (2013.01)

(58) Field of Classification Search
CPC .............. A61B 17/8635; A61B 17/864; A61B 17/1615; A61B 17/863; A61B 17/8625
See application file for complete search history.

(56) References Cited

U.S. PATENT DOCUMENTS

| | | | | |
|---|---|---|---|---|
| 5,098,435 | A * | 3/1992 | Stednitz | A61B 17/1637 606/907 |
| 8,945,193 | B2 * | 2/2015 | Kirschman | A61B 17/8841 606/317 |
| 11,273,043 | B1 * | 3/2022 | Abbasi | A61B 17/1757 |
| 2017/0360490 | A1 * | 12/2017 | Reed | A61B 17/863 |
| 2020/0375750 | A1 * | 12/2020 | Abbasi | A61F 2/4603 |

* cited by examiner

*Primary Examiner* — Kevin T Truong
*Assistant Examiner* — Diana Jones
(74) *Attorney, Agent, or Firm* — Michael D. Eisenberg

(57) ABSTRACT

A self-drilling bone screw, comprising a head, a threaded body, and a tip region. The threaded body extends vertically below the head and has a helical male threading. The tip region extends vertically below the treaded body. The tip region is fluted and has a pointed bottom tip, such that the tip region is configured to drill a hole into a bone and generate bone chips. The tip region further has a slot disposed horizontally through a portion of the tip region above the pointed bottom tip, the slot being configured to trap at least some of the bone chips, thereby enabling fusion between the bone and the bone chips. A diameter of threaded body is larger than a maximal diameter of the tip region.

14 Claims, 12 Drawing Sheets

BONE SCREW WITH A SLOTTED SELF-DRILLING TIP

TECHNICAL FIELD

The present invention, in some embodiments thereof, relates to medical devices, more specifically, to bone screws.

BACKGROUND OF THE INVENTION

Bone screws are medical screws configured to drill into bones and remain joined to bones. Bone screws are implants inserted into the bone to immobilize fractured bone segments to aid in the healing process, and as an adjunct to spine fusion surgery to help hold implants in place.

Many existing bone screws need locking mechanisms to secure the screw to the bone and retain the screw in the bone. Other bone screws are hollow and include bores at the bottom end of the screw to receive biological material as the screws are drilled into the bones. These bone screws have fenestrations configured to encourage fusion between the bone outside the screw and the biological material inside the screw. The fusion locks the screw in place.

For example, U.S. Pat. No. 8,945,193 to Kirschman relates to a system comprising a screw element having a generally cylindrical body having a bore or lumen therethrough and a plurality of fenestrations or windows through which biological material may be provided. The system comprises a tool for inserting the biological material into the screw element so that the biological material may extrude through the plurality of fenestrations or windows and through an aperture in the tip of the screw element thereby enabling providing a fusion mass across two adjacent facet bones or a facet joint wherein the screw itself provides both a fixation component and a screw component.

BRIEF SUMMARY OF EMBODIMENTS OF THE INVENTION

The inventor has found that hollow screws with fenestration along the threaded are structurally weaker than screws without fenestrations. Moreover, a screw with a bore at the tip is not very efficient at burrowing into the bone and create small enough bone chips to be used as biological material. Finally, once the screw is fixed to the bone via fusion, removal of the screw from the bone is challenging.

An aim of the present invention is to provide a bone screw that encourages fusion between biological material and bones, but which does not have the disadvantages described above.

Therefore, an aspect of the present invention relates to a self-drilling bone screw, comprising a head, a threaded body, and a tip region. The threaded body extends vertically below the head and has a helical male threading. The tip region extends vertically below the treaded body. The tip region is fluted and has a pointed bottom tip, such that the tip region is configured to drill a hole into a bone and generate bone chips. The tip region further has a slot disposed horizontally through a portion of the tip region above the pointed bottom tip, the slot being configured to trap at least some of the bone chips, thereby enabling fusion between the bone and the bone chips. A diameter of threaded body is larger than a maximal diameter of the tip region.

In a variant, the tip region has a top portion and a bottom portion. The top portion is a fluted cylinder or a fluted frusto-cone, and includes the slot horizontally traversing the fluted cylinder or a fluted frusto-cone. The bottom portion is a fluted cone extending downward from a bottom end of the top portion and ending into the pointed bottom edge. Fluting on the top portion and on the bottom portion comprises two symmetrically-extending flutes carved out of the top portion and the bottom portion. Two uncarved lands extend between the two flutes. Two lips are formed, each lip extending from an edge of a respective flute having smallest radius to a respective land, each lip being at an angle with the respective flute. Edges at which the lands and the lips connect are cutting edges.

In another variant, the slot extends between a first front end and a rear end of the tip region, such that the slot intersects a first one of the cutting edges at the front end, and that the slot intersects a second one of the cutting edges at the rear end.

In yet another variant, the slot traverses the tip portion from and has a first end inside opening at a first one of the flutes and a second end opening at a second one of the flutes, such that the slot does not intersect the cutting edges.

In a further variant, each of the flutes comprises a curved, downward-facing surface above the slot, the curved, downward-facing surface extending radially outward from above the slot on at least one side of the slot, the curved surface being configured to trap the bone chips in a vicinity of the slot and thereby enhance the fusion.

In yet a further variant, the curved surface is a concave surface.

In a variant, the portion of the tip region below the slot is solid.

In another variant, the head comprises an aperture. A hollow channel extends from the aperture, through the head, the body, and a portion of the tip region until the slot, such that the hollow channel in in fluid communication with the slot. The portion of the tip region below the slot is solid.

In yet another variant, the self-drilling bone screw further includes a drill bit configured to be inserted into the hollow channel via the aperture on the head and to drill into the fused bone chips and bone in the slot for removal of the self-drilling bone screw from the bone. The solid portion of the tip region below the slot is configured to prevent the drill bit from drilling beyond a bottom end of the slot.

In a further variant, the head, the treaded body, and the tip region are integral with each other.

In yet a further variant, a diameter of the head is larger than the diameter of the threaded body.

In a variant, a diameter of the head is smaller to or equal to the diameter of the threaded body.

In another variant, for each uncarved land, an interface between the section of the uncarved land located on the top portion and a continuation of the uncarved land extending in the bottom portion is helical.

In yet another variant, for each interface: a distance between the interface and the pointed tip is highest at a first location where the interface directly meets the flute and is lowest at second location where the interface meets the cutting edge; the distance between the interface and the pointed tip decreases as the interface extends from the first location to the second location.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 1:
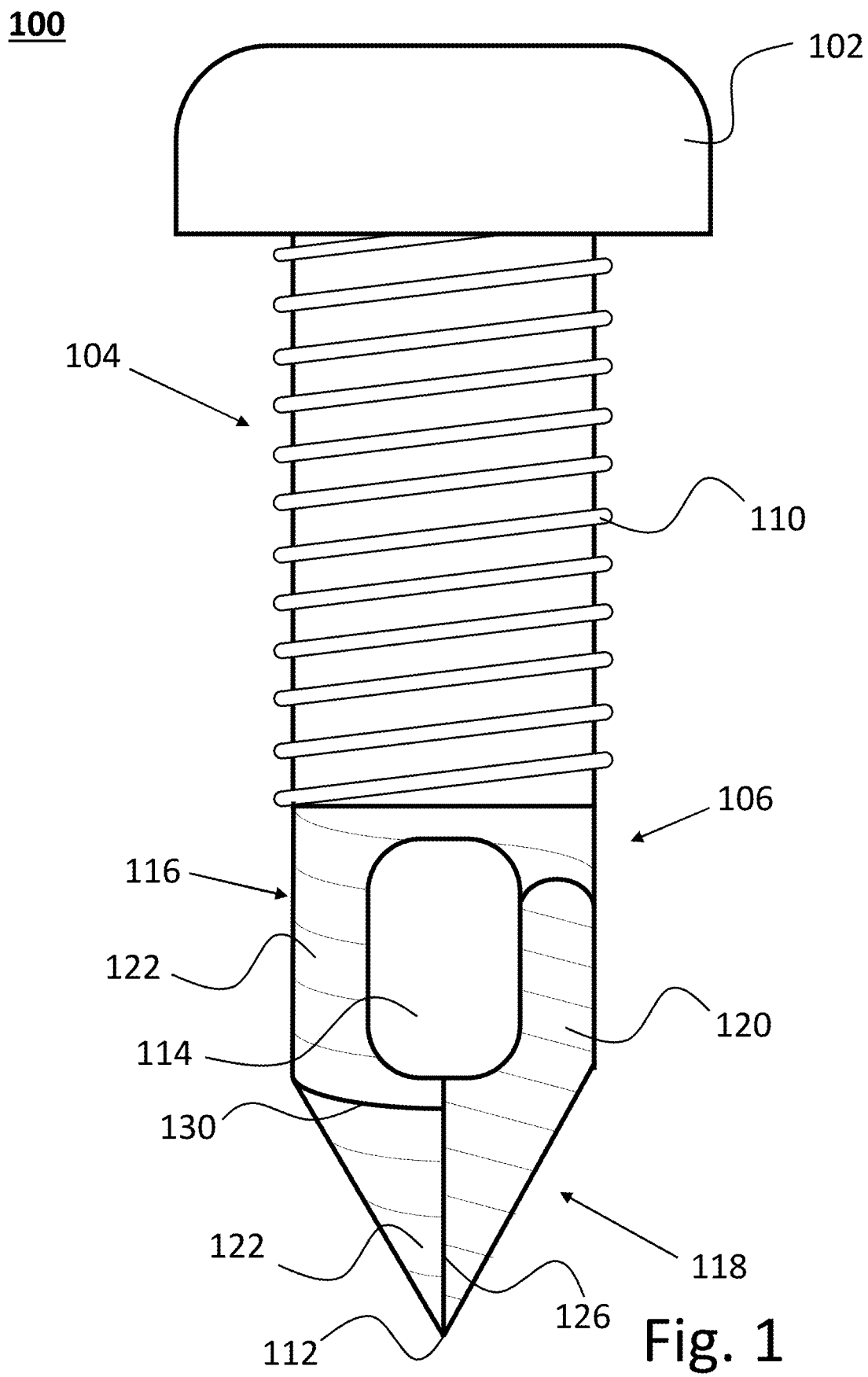
FIG. 1 is a front view of a bone screw having a self-drilling tip region extending vertically and having a horizontal slot therethrough, according to some embodiments of the present invention.
Figure 2:
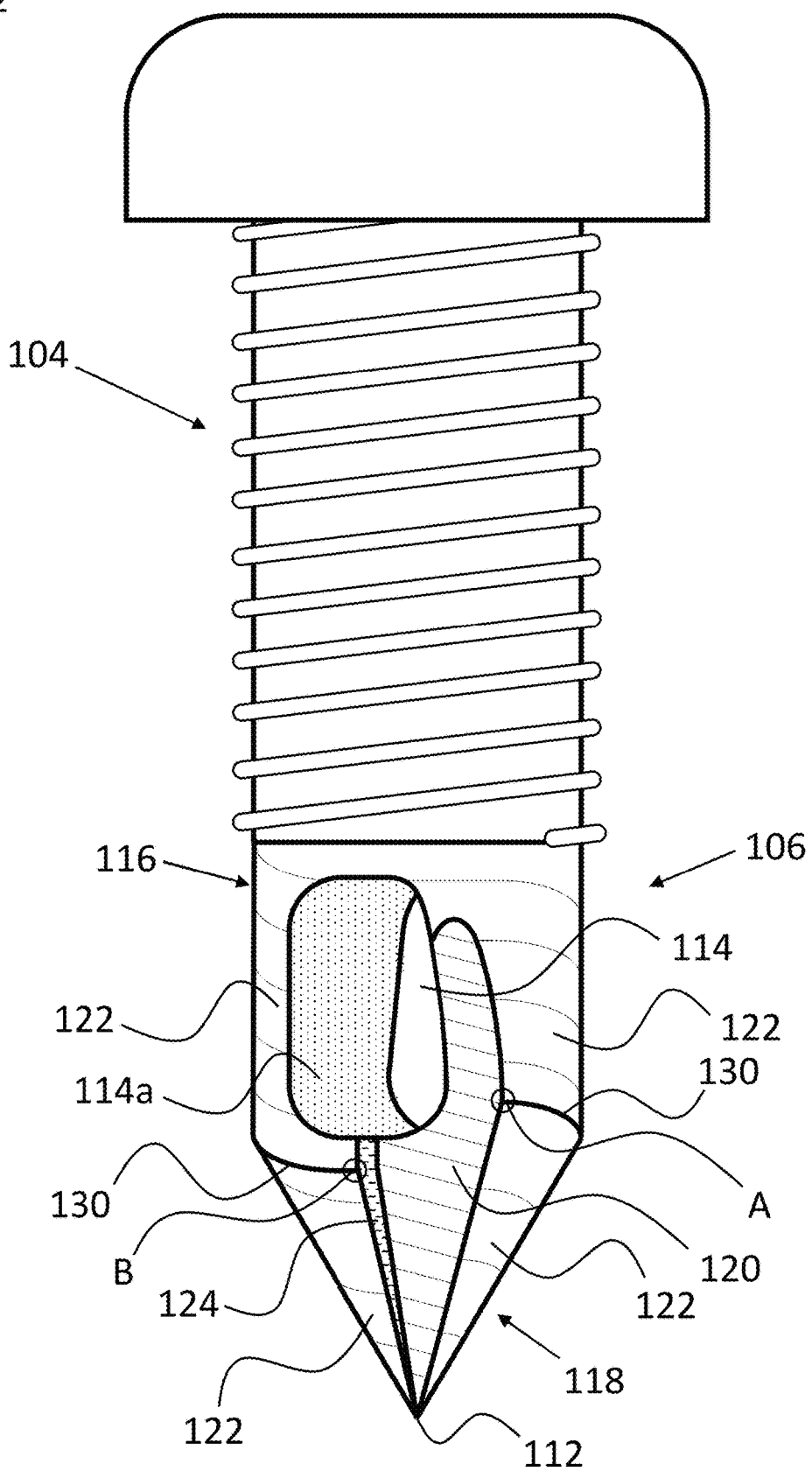
FIG. 2 shows the bone screw of FIG. 1 rotated to show a flute carved out of a tip region of the bone screw between two uncarved lands, according to some embodiments of the present invention.
Figure 3:
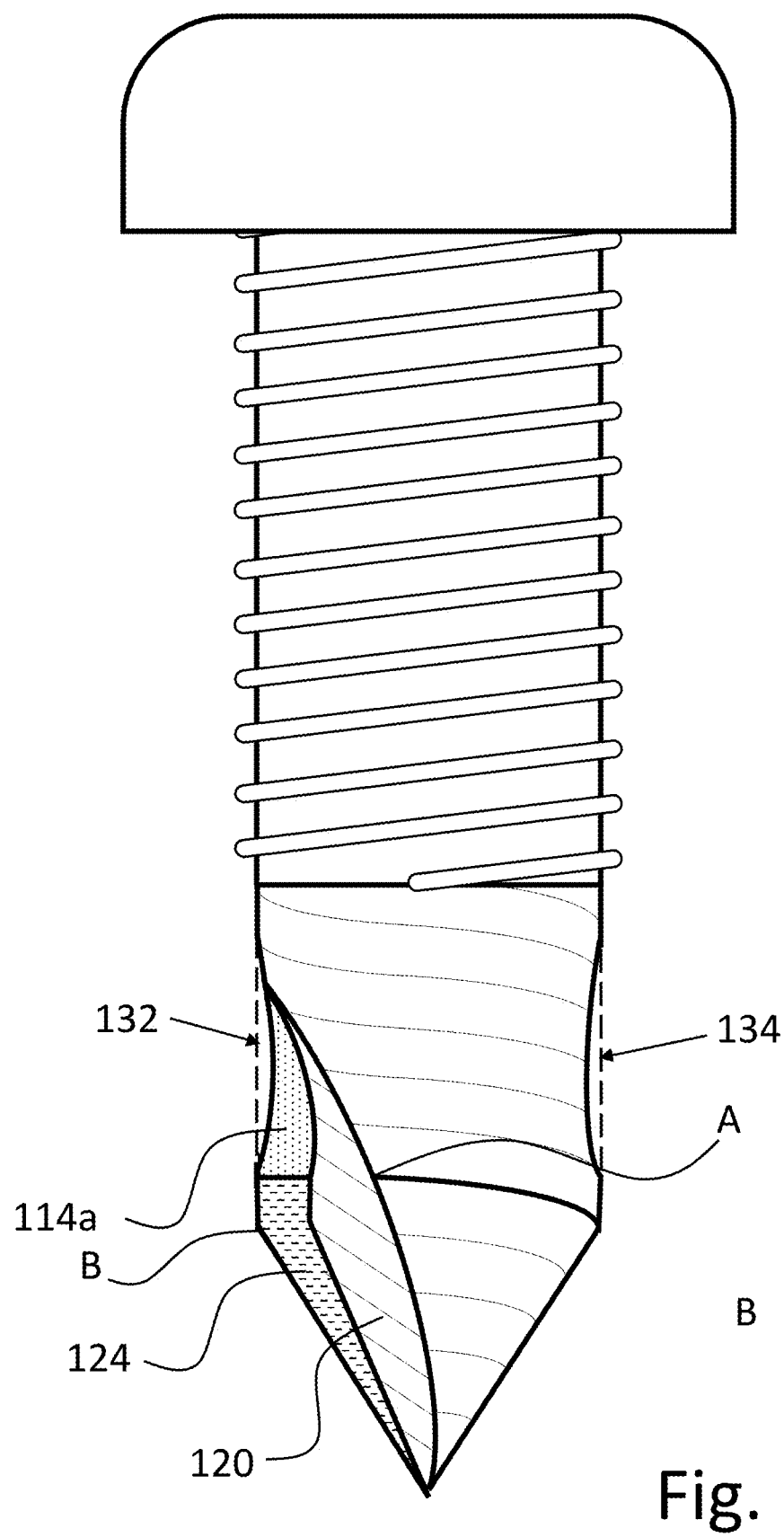
FIG. 3 is a side view of the bone screw of FIG. 1, showing the lateral ends of the channel, according to some embodiments of the present invention.
Figure 4:
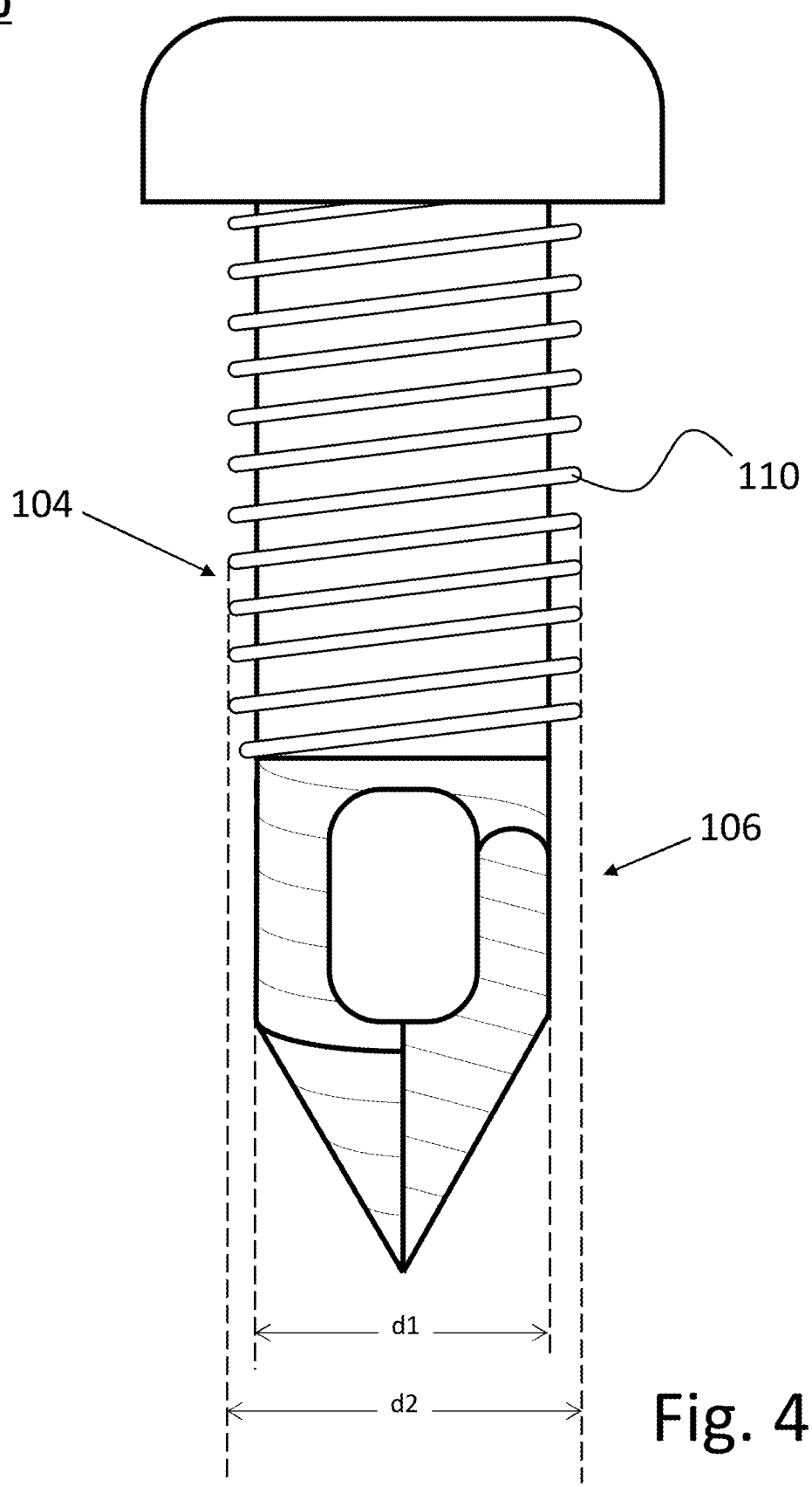
FIG. 4 is a front view of the bone screw of FIGS. 1-3, showing the diameters of the body and of the tip region.
Figure 5:
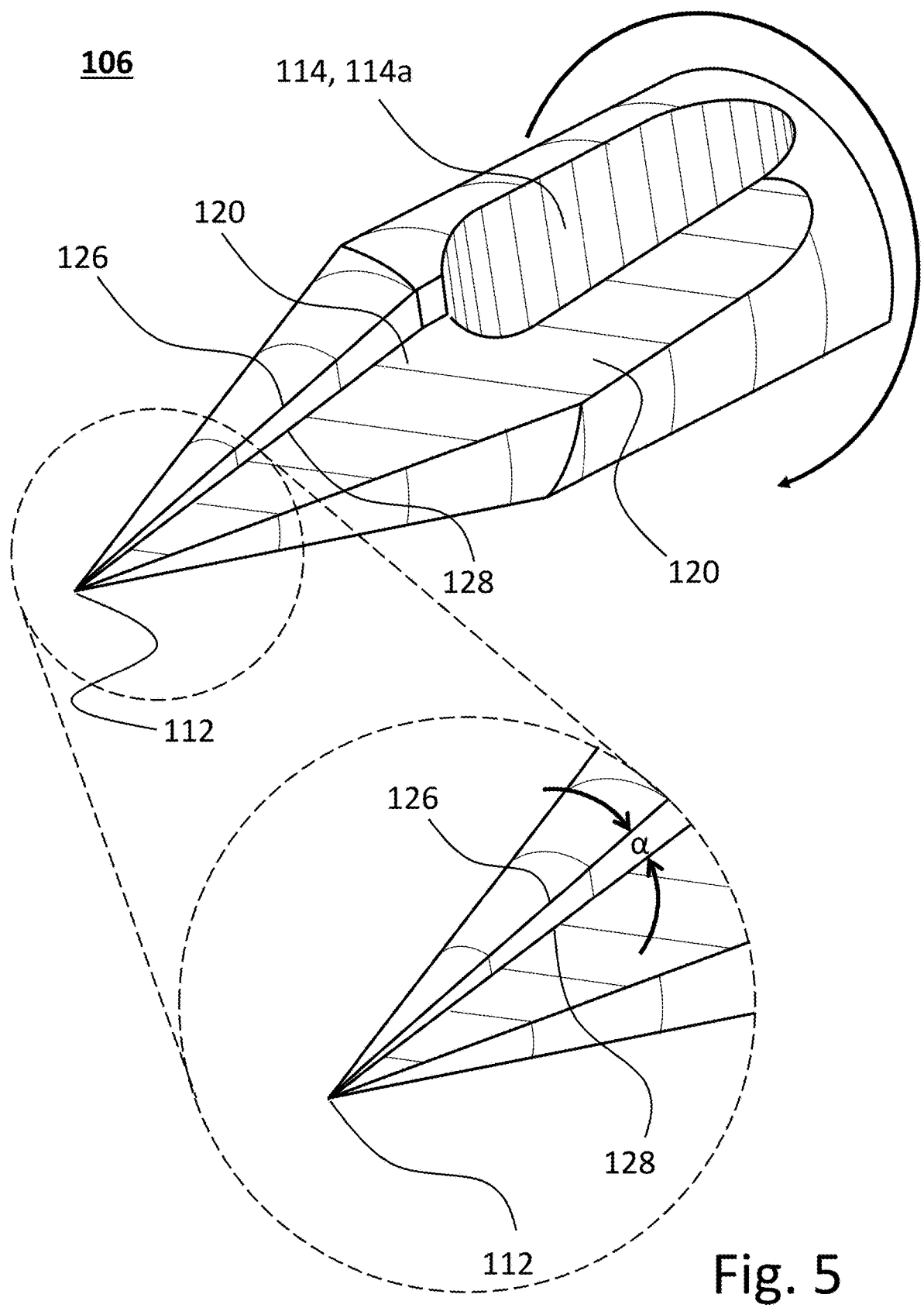
FIG. 5 is a perspective view of the self-drilling tip region of the bone screw of FIGS. 1-4, according to some embodiments of the present invention.

Referring now to the figures, FIG. 1 is a front view of a bone screw having a self-drilling tip region extending vertically and having a horizontal slot therethrough, according to some embodiments of the present invention. FIG. 2 shows the bone screw of FIG. 1 rotated to show a flute carved out of a tip region of the bone screw between two uncarved lands, according to some embodiments of the present invention. FIG. 3 is a side view of the bone screw of FIG. 1, showing the lateral ends of the channel, according to some embodiments of the present invention. FIG. 4 is a front view of the bone screw of FIGS. 1-3, showing the diameters of the body and of the tip region; FIG. 5 is a perspective view of the self-drilling tip region of the bone screw of FIGS. 1-4, according to some embodiments of the present invention.

The self-drilling bone screw 100, includes—from top to bottom—a head 102, a threaded body 104, and a tip region 106. The head 106 includes a drive slot 108 (shown in FIG. 5), configured to receive a screwdriver tip. The threaded body 104 extends vertically below the head 102 and has a male helical thread 110. The body may be cylindrical of frusto-conical, for example.

The tip region 106 extends vertically below the body 104, ends in a pointed bottom tip 112. Furthermore, the tip region 106 is fluted, such that the tip region 106 is configured to drill a hole into a bone and generate bone chips. The tip region has a slot 114 disposed horizontally through a portion of the tip region 106 above the pointed bottom tip 112. The slot 114 is configured to trap at least some of the bone chips generated during the drilling. In this manner, fusion between the bone and the bone chips occurs to lock the bone screw in place. In a variant, the head 102, body 104, and the tip region 106 are integral with each other and may be manufactured from a single piece of material.

As seen in FIG. 4, the tip 106 region has a maximal diameter d1, while the body 104 has a diameter d2 defined as double the distance between the center of the body and the outer end of the thread 110. It should be noted that if the body 104 is cylindrical, d2 is constant throughout the length of the cylinder. If the body 104 is frusto-conical, d2 is smaller at the bottom of the body 104. In either case, the diameter d2 of the body 104 is always larger than the maximal diameter d1 of the tip region. In this manner, the thread 110 can creates a corresponding female thread in the bone as the drilling occurs, thereby generating a better hold of the bone screw 100 on the bone.

In some embodiments of the present invention, the tip region 106 includes a top portion 116 and a bottom portion 118. The top portion 116 is a fluted cylinder or a fluted frusto-cone, and includes the slot 114 which horizontally traverses the fluted cylinder or a fluted frusto-cone. The bottom portion 118 is a fluted cone extending downward from a bottom end of the top portion 116 and ending into the pointed bottom edge 112.

The fluting on the top portion and on the bottom portion comprises two symmetrically-extending flutes 120 carved out of the top portion and the bottom portion. Two uncarved lands 122 extend between the two flutes. More specifically, each uncarved lands 122 is adjacent to two flutes 120, and each flute 120 is adjacent to two uncarved lands 122.

Two lips 124 are formed, each extending from an edge of a respective flute 120 having smallest radius to a respective land 122. Each lip extends at an angle from the respective flute. The edges at which the lands 122 and the lips 124 connect are cutting edges 126 and perform the cutting of the bone, much like the cutting edges of a self-drilling screw.

The angle α between an inner edge 128 and the cutting edge 126 of the lip 124 depends upon the hardness of the bone that is to be drilled into. Generally, harder bones require smaller angles. Therefore, different bone screws of the present invention may be produced to match different bones to be drilled into. In some non-limiting examples, the angle α may be between 2 and 10 degrees.

In some embodiments of the present invention the interface 130 between the top portion 116 and the bottom portion 118 is helical. More specifically, the interface between the section of an uncarved land 122 located on the top portion 116 and the continuation of the same uncarved land 122 extending in the bottom portion 118 is helical. In some embodiments of the present invention, for each interface 130, the distance between the interface 130 and the pointed tip 112 is highest at a first location A where the interface 130 directly meets the flute 120 and is lowest at second location B where the interface 130 meets the corresponding cutting edge 126. The distance between the interface and the pointed tip 112 decreases, as the interface extends from location A to location B. In this manner, the pitch of the helical interface 130 generates a cutting angle to enable cutting through the bone. Higher pitches may be better adapted for cutting into harder bones, while lower pitches (above 0 degrees) may be better adapted for cutting into softer bones.

In some embodiments of the present invention, the slot 114 extends between a front end 132 and a second rear end 134 of the tip region 106, such that the slot 114 intersects a first one of the cutting edges 126 at the front end 132, and a second one of the cutting edges (not drawn) at the rear end 114. In this manner, once the cutting edges 126 cut the bone and generate bone chips, the bone chips are directed by the flutes 120 and the lips into the slot 114. The fuller the slot 132 is with bone chips, the more effective the fusion between bone chips in the slot and bone outside the slot is.

The slot has 114 a wall 114a. Due to the flutes 120 being carved out of the tip region 105, a portion of the slot's wall 114a can be seen extending outward from the side of the screw 100 and this further helps to guide the bone chips into the slot 114.

Relative to the described prior art, the bone screw 100 of the present invention is structurally stronger, since there are no fenestrations in the threaded body 104, and since the bottom portion 118 below the slot 114 is solid (not hollow). Moreover, the bottom tip 112 is pointed and better suited to perforate the bone and burrow though the bone than a bored screw. As the bone screw 100 rotates inside the bone, the lip 124 and the cutting edge 126 efficiently produce small bone chips, which are small enough to be conducted into the slot and to easily fuse with each other and with the bone outside the screw 100.

Figure 11:
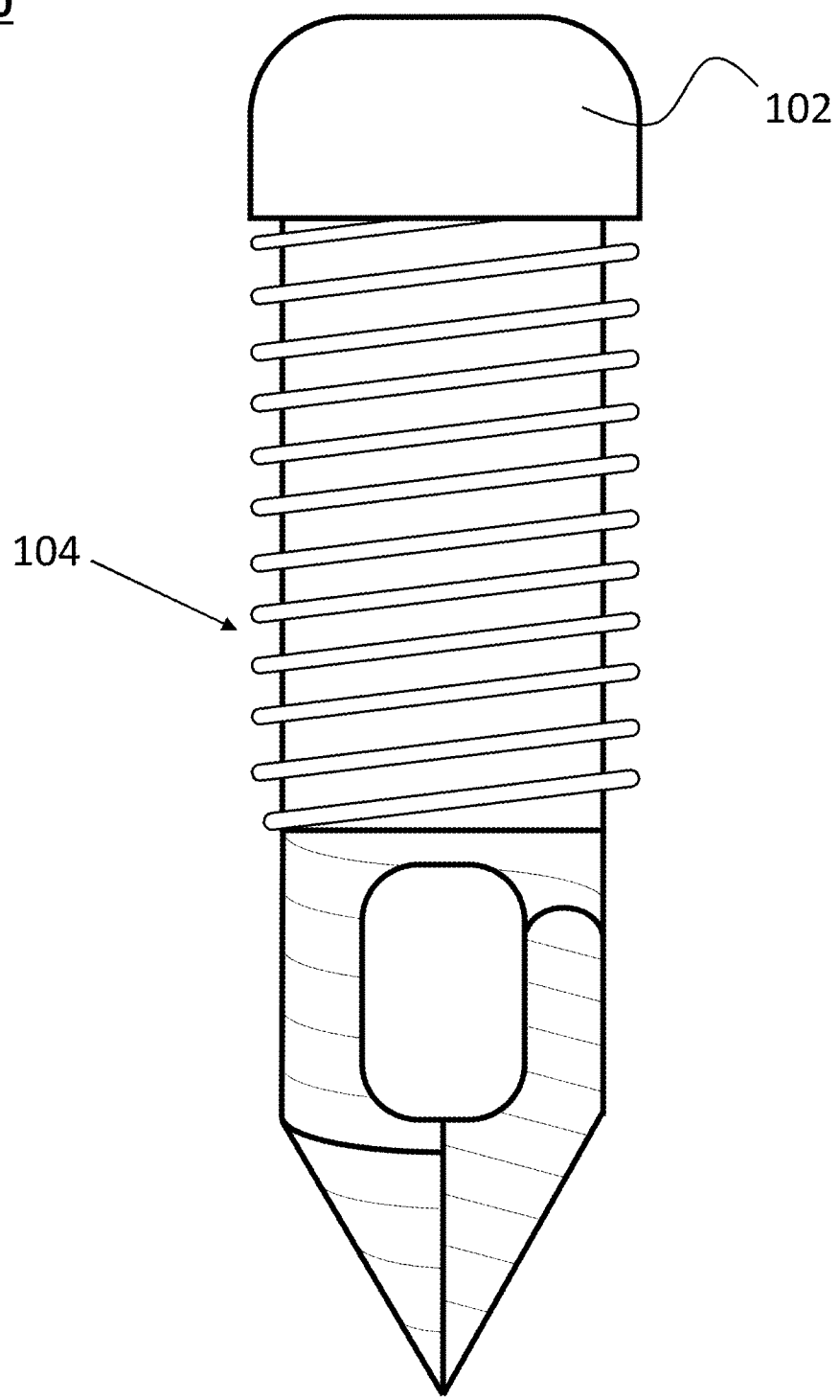
FIG. 11 illustrates a bone screw having a head with a diameter equal to a diameter of the threaded body.
Figure 12:
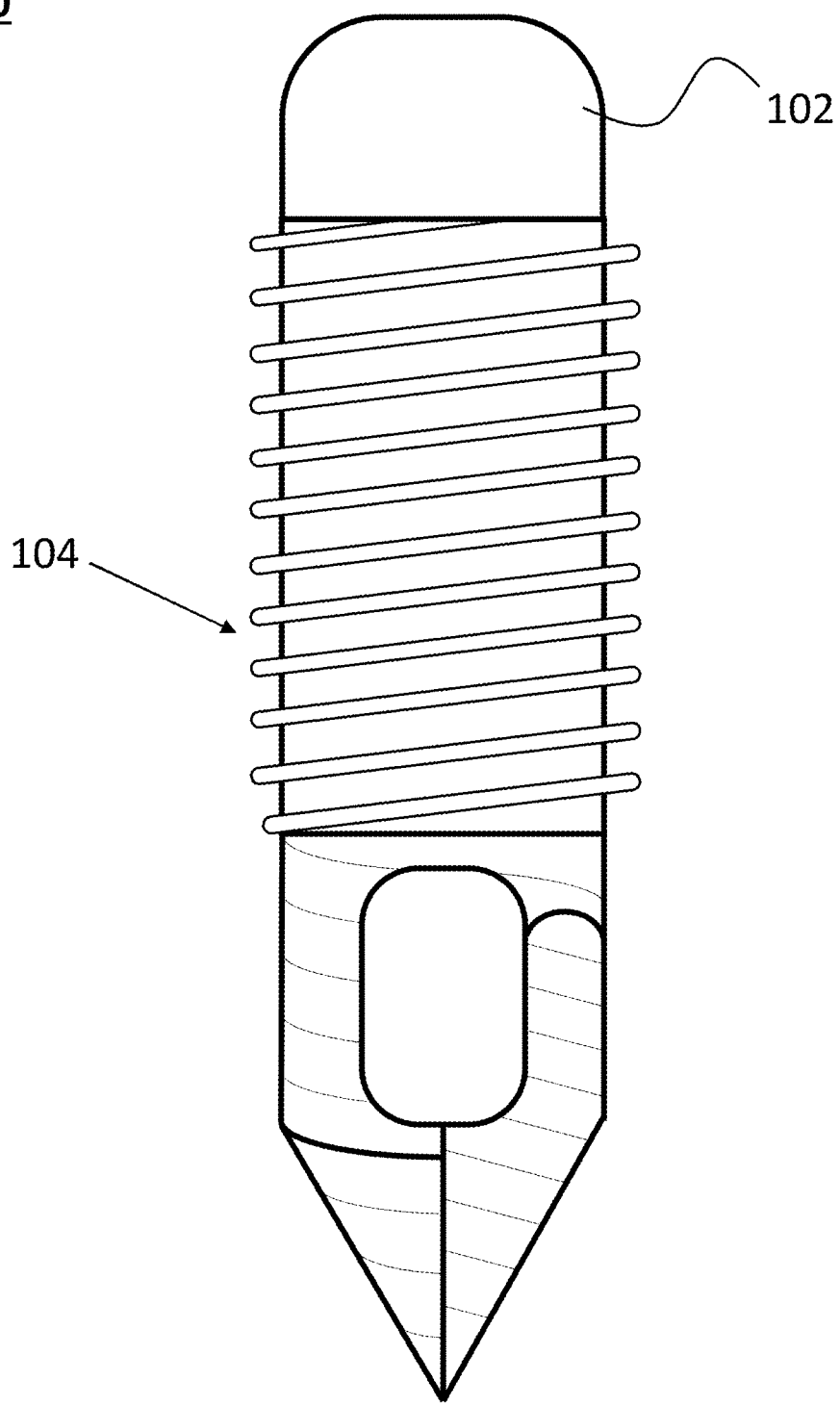
FIG. 12 illustrates a bone screw having a head with a diameter smaller than a diameter of the threaded body.

While the head 102 is shown herein to be larger than the threaded body 104, this is not a necessity. In fact, the head 102 may have the same size of or be smaller than the threaded body 104, as shown in FIGS. 11 and 12, respectively. In this manner, the bone screw may be used a permanent implant. In some embodiments of the present invention, the shape of the head 102 is design to fit and be joined with an external object to secure the external object to the bone. For example, the external object may be a fake tooth configured to be secured to a patient's body via bone screw 100.

Figure 6:
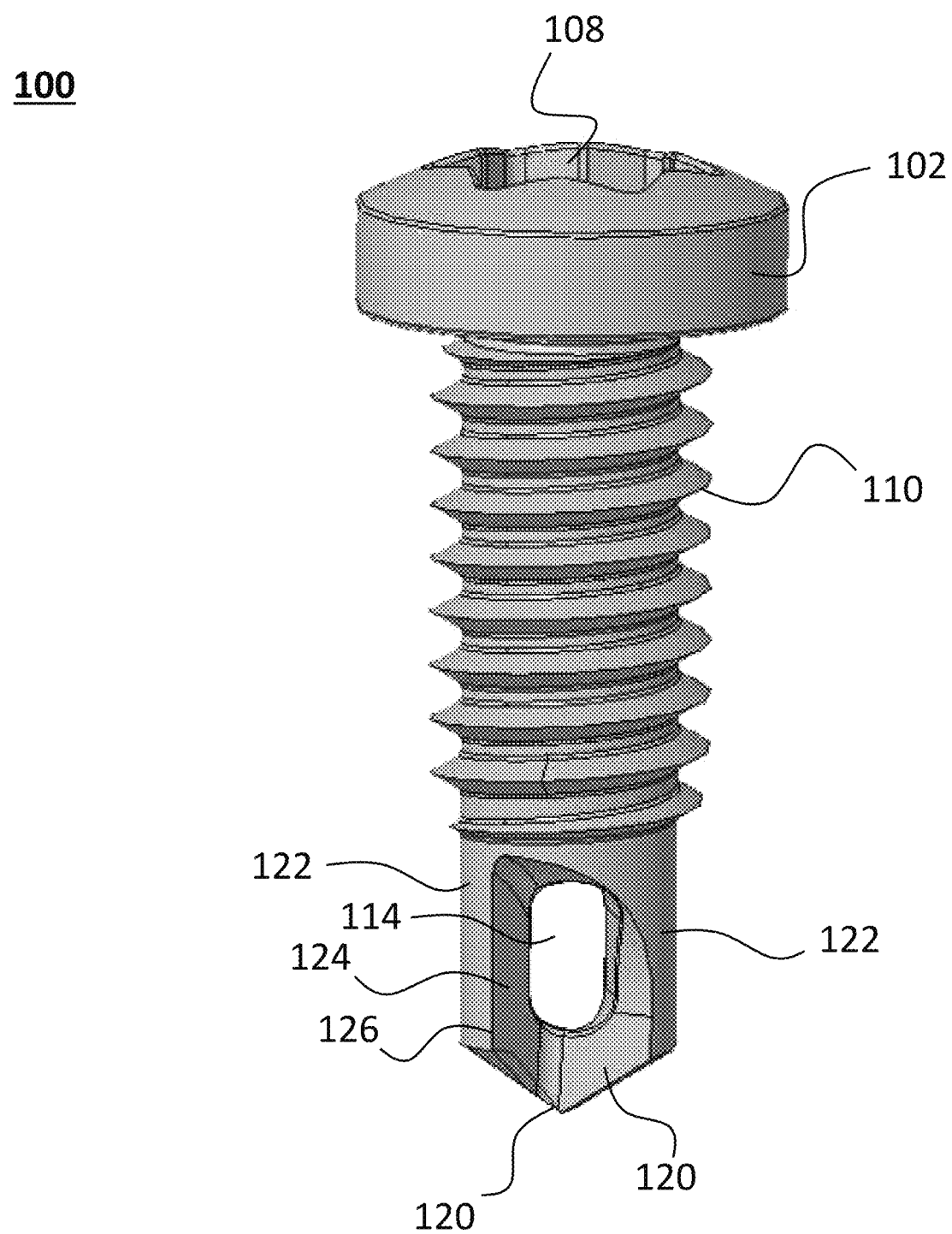
FIG. 6 illustrates a bone screw in which the channel traverses the flutes and not the lands, according to some embodiments of the present invention.
Figure 7:
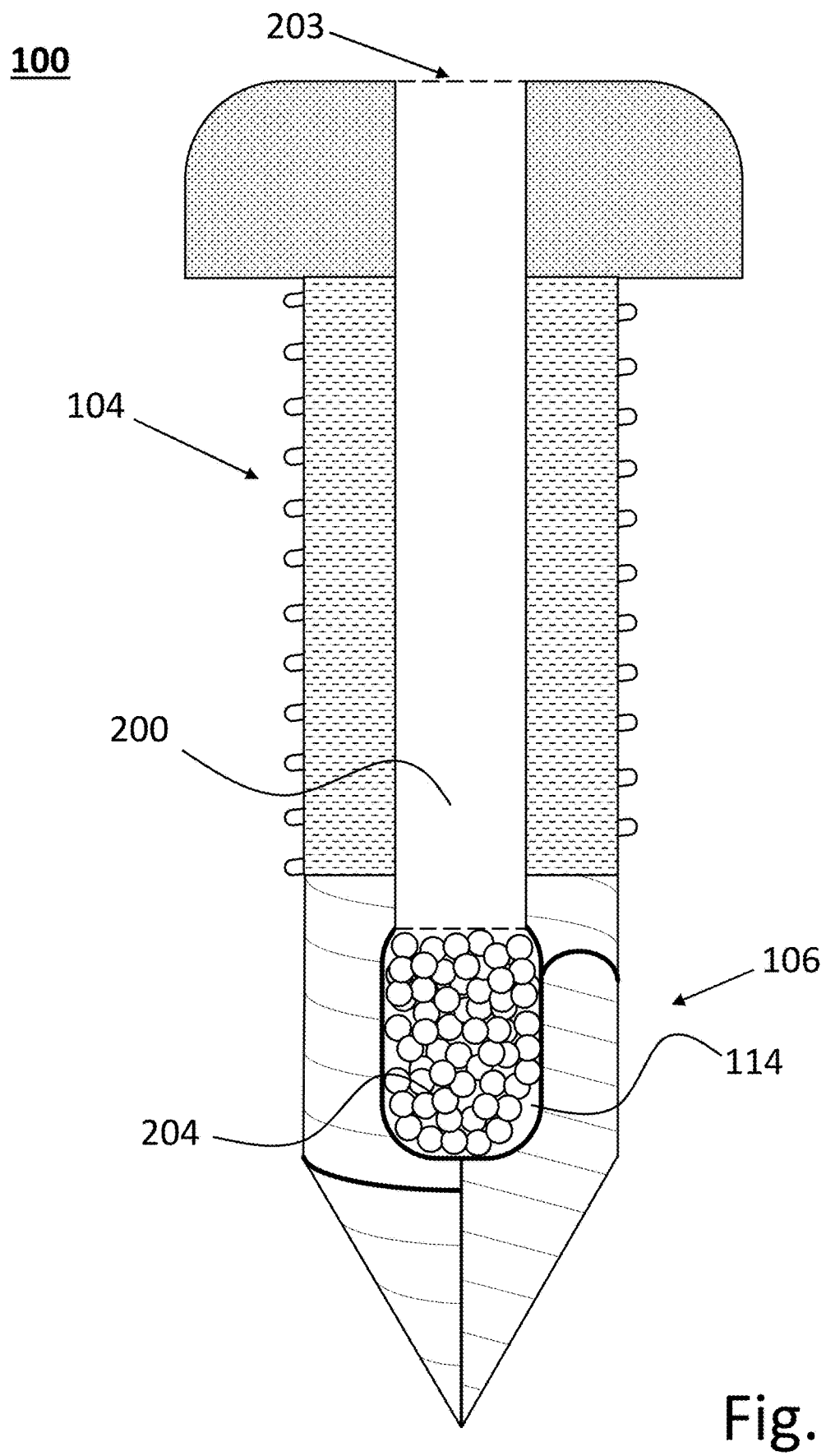
FIGS. 7-10 illustrate a bone screw having a hollow channel extending therethrough and communicating with the slot above the slot, according to some embodiments of the present invention.

FIG. 6 illustrates a bone screw in which the slot traverses the flutes and not the lands, according to some embodiments of the present invention.

In the example of FIG. 6, the bone screw 100 is similar to the bone screw 100 of FIGS. 1-5. The difference lies in the face that the slot 114 in FIG. 5 does not intersect the cutting edges 126, nor does the slot 114 intersect the lands 122. Rather, the slot 114 traverses the tip portion has a first end opening at a first one of the flutes and a second end opening at a second one of the flutes.

In some embodiments of the present invention, each of the flutes 120 includes a curved, downward-facing surface 136 above the slot 114. The curved, downward-facing surface 136 extending radially outward from above the slot 114 on at least one side of the slot 114, and is configured to trap the bone chips in the flute 120, near of the slot 114 and thereby enhance the fusion of the bone chips with the surrounding bone. In a variant, the curved surface 136 is concave to better trap the bone chips.

FIGS. 7-10 illustrate a bone screw having a hollow channel extending therethrough and communicating with the slot above the slot, according to some embodiments of the present invention.

In some embodiments of the present invention, the bone screw 100 includes a hollow channel 200, which extends through the head 102, the body 104 and a portion of the tip region 106 until the slot 114, such that the hollow channel 200 in in fluid communication with the slot 114. The portion of the tip region below the slot 114 is solid (not hollow).

Figure 8:
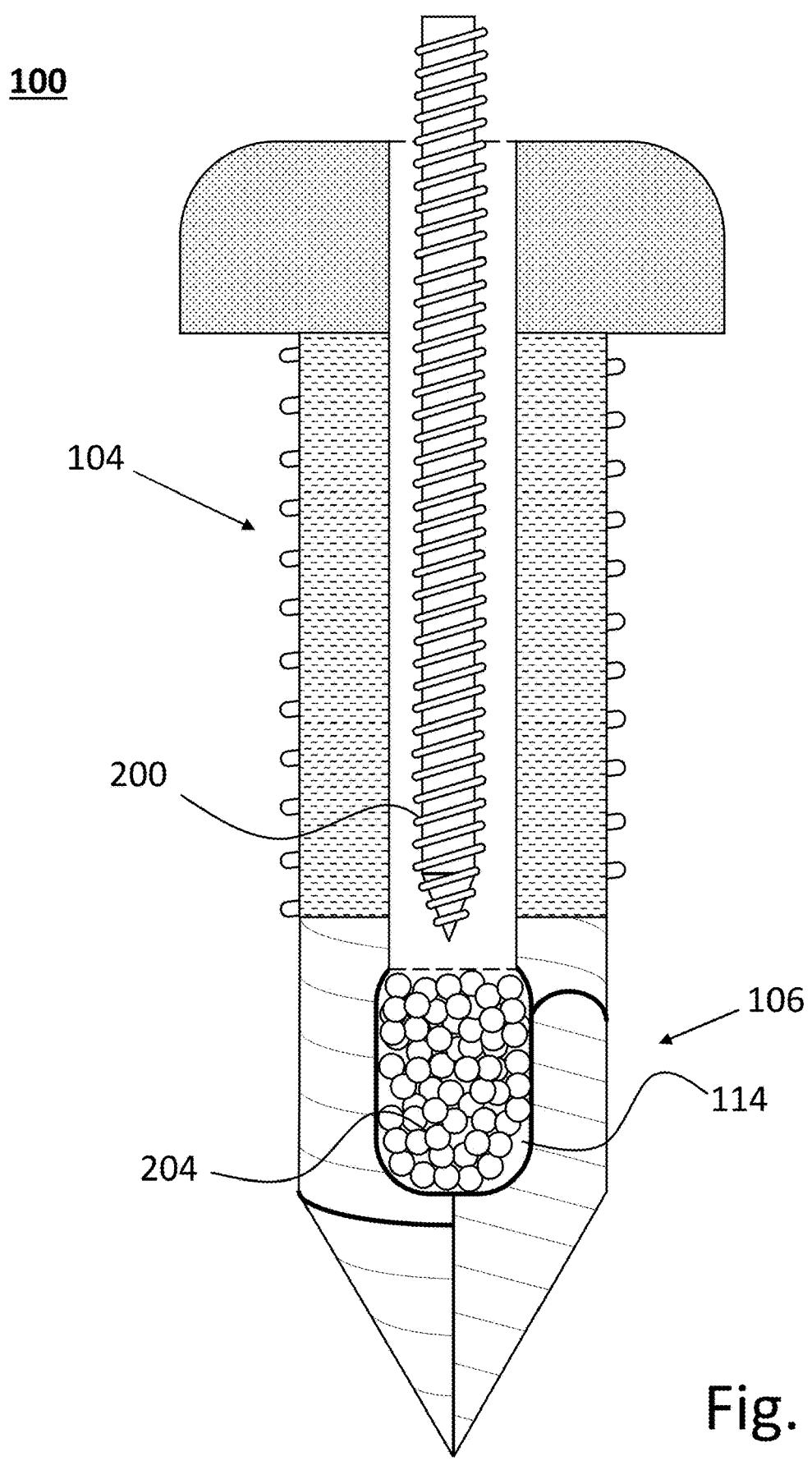
Figure 9:
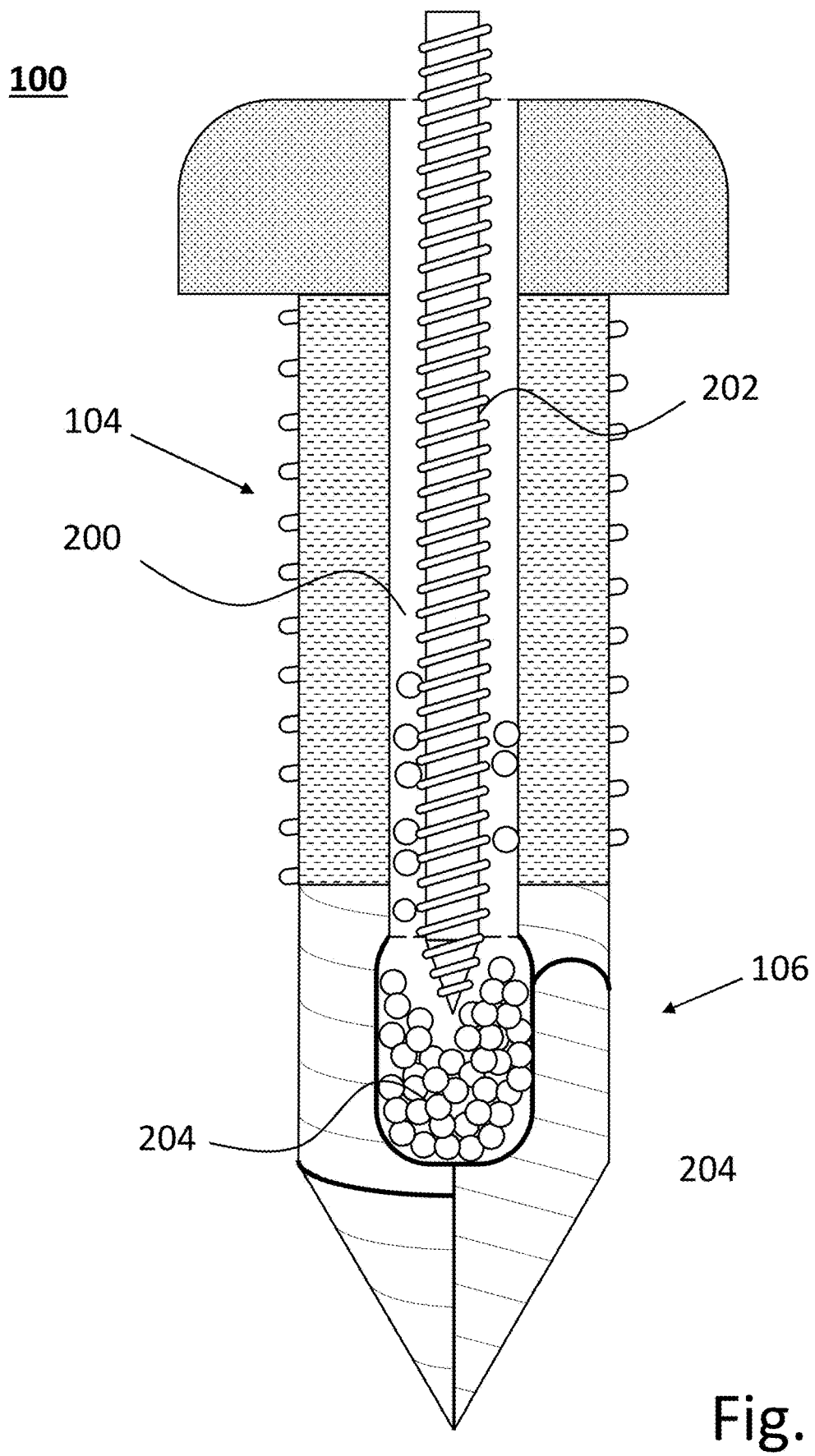
Figure 10:
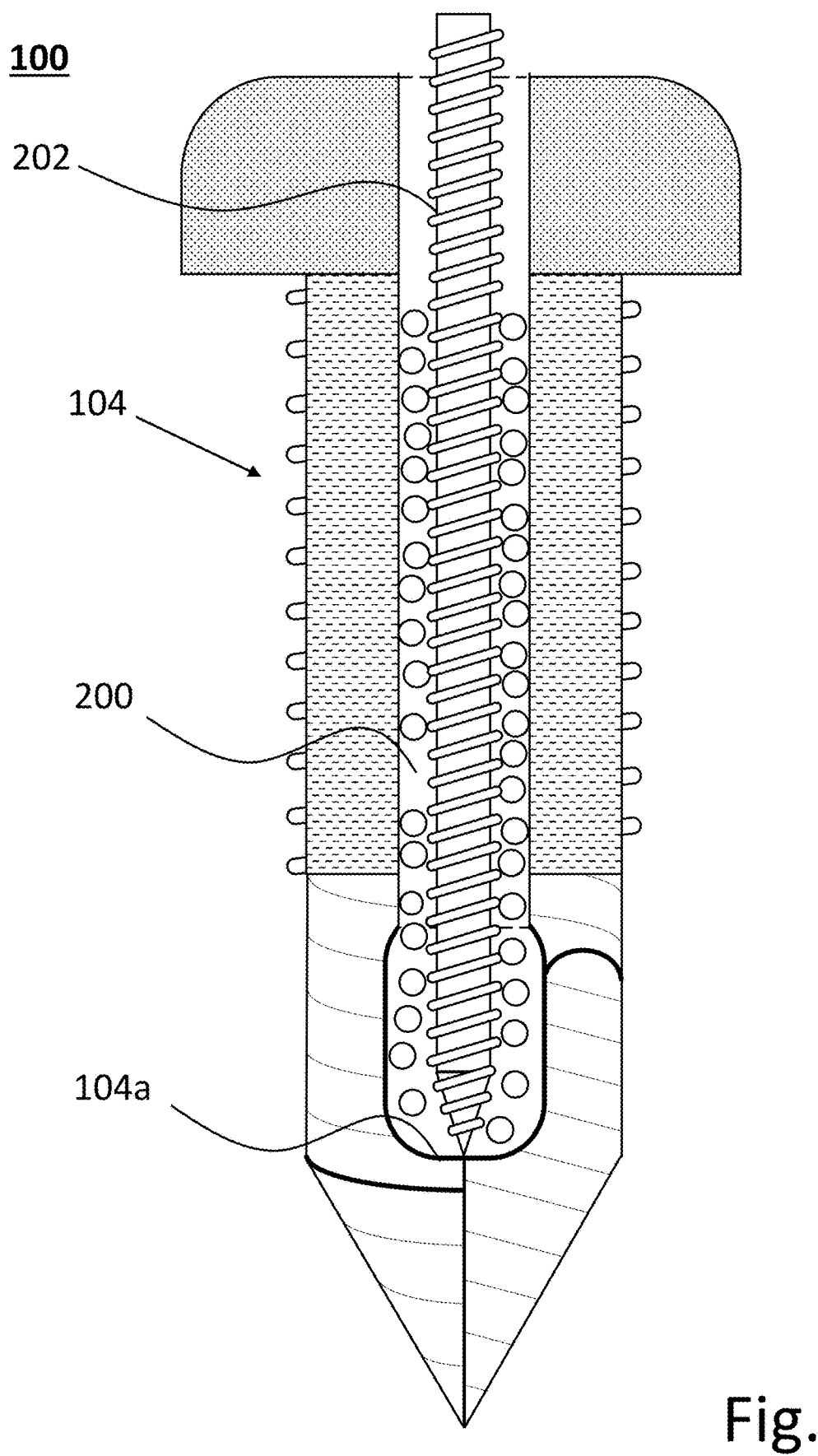

The head 102 has an aperture 203 that allow access to the channel 200. In this manner, a drill bit 202 can be inserted through the aperture 203 into the hollow channel 200, to drill into the fused bone chips 204 and bone in the slot 114 for removal of the self-drilling bone screw 100 from the bone (FIG. 8). The drill bit has a diameter that is smaller than the smallest horizontal dimension (e.g., a diameter) of the hollow channel 200. The bone chips drilled by the drill bit 202 are removed by traveling via the channel 200 as they are pushed by the rotation of the threads of the drill bit 202 (FIGS. 9-10).

As seen on FIG. 10, the solid portion of the tip region below the slot 114 is configured to prevent the drill bit 202 from drilling beyond a bottom end of the slot. In this manner, the bone chips in the slot can be safely drilled, without the risk of drilling beyond the tip region 106 and into the bone, and unnecessarily damaging healthy bone. This is another advantage of the present invention with respect to prior art in which bone screws have bores opening at the bottom ends thereof.

Regarding all the above figures, it should be noted that the dimensions of the bone screw 100 may be varied to fit different uses and to drill to different types of bones.

What is claimed is:

1. A self-drilling bone screw, comprising:
   a head;
   a threaded body extending vertically below the head and having a helical male threading;
   a tip region extending vertically below the threaded body, the tip region being fluted and having a pointed bottom tip, such that the tip region is configured to drill a hole into a bone and generate bone chips, the tip region further having a slot disposed horizontally through a portion of the tip region above the pointed bottom tip, the slot being configured to trap at least some of the bone chips, thereby enabling fusion between the bone and the bone chips,
   wherein:
   a diameter of the threaded body is larger than a maximal diameter of the tip region;
   the tip region has a top portion and a bottom portion;

the top portion is a fluted cylinder or a fluted frusto-cone, the top portion including the slot horizontally traverses the fluted cylinder or the fluted frusto-cone;

the bottom portion is a fluted cone extending downward from a bottom end of the top portion and ending into the pointed bottom tip;

fluting on the top portion and on the bottom portion comprises two flutes carved out of the top portion and the bottom portion;

two uncarved lands extend between the two flutes;

two lips are formed, each lip extending from an edge of a respective flute having smallest radius to a respective land, each lip being at an angle with the respective flute;

edges at which the lands and the lips connect are cutting edges.

2. The self-drilling bone screw of claim 1, wherein the two flutes extend symmetrically.

3. The self-drilling bone screw of claim 1, wherein the slot extends between a first front end and a rear end of the tip region, such that the slot intersects a first one of the cutting edges at the first front end, and that the slot intersects a second one of the cutting edges at the rear end.

4. The self-drilling bone screw of claim 1, wherein the slot traverses the tip portion and has a first end opening at a first one of the flutes and a second end opening at a second one of the flutes, such that the slot does not intersect the cutting edges.

5. The self-drilling bone screw of claim 4, wherein each of the flutes comprises a curved, downward-facing surface above the slot, the curved, downward-facing surface extending radially outward from above the slot on at least one side of the slot, the curved, downward-facing surface being configured to trap the bone chips in a vicinity of the slot and thereby enhance the fusion.

6. The self-drilling bone screw of claim 5, wherein the curved, downward-facing surface is a concave surface.

7. The self-drilling bone screw of claim 1, wherein the portion of the tip region below the slot is solid.

8. The self-drilling bone screw of claim 1, wherein:
the head comprises an aperture;
a hollow channel extends from the aperture, through the head, the threaded body, and the portion of the tip region to the slot, such that the hollow channel is in fluid communication with the slot;
the portion of the tip region below the slot is solid.

9. The self-drilling bone screw of claim 8, further comprising:
a drill bit configured to be inserted into the hollow channel via the aperture on the head and to drill into the bone chips and bone in the slot for removal of the self-drilling bone screw from the bone;
wherein the solid portion of the tip region below the slot is configured to prevent the drill bit from drilling beyond a bottom end of the slot.

10. The self-drilling bone screw of claim 1, wherein the head, the threaded body, and the tip region are integral with each other.

11. The self-drilling bone screw of claim 1, wherein a diameter of the head is larger than the diameter of the threaded body.

12. The self-drilling bone screw of claim 1, wherein a diameter of the head is smaller than or equal to the diameter of the threaded body.

13. The self-drilling bone screw of claim 1, wherein for each uncarved land, an interface between a section of the uncarved land located on the top portion and a continuation of the uncarved land extending in the bottom portion is helical.

14. The self-drilling bone screw of claim 13, wherein, for each interface:
a distance between the interface and the pointed bottom tip is highest at a first location where the interface directly meets the flute and is lowest at second location where the interface meets its cutting edge;
the distance between the interface and the pointed bottom tip decreases as the interface extends from the first location to the second location.

* * * * *